United States Patent [19]

Gosser

[11] 4,303,632
[45] Dec. 1, 1981

[54] PREPARATION OF HYDROGEN PEROXIDE

[75] Inventor: Lawrence W. Gosser, Wilmington, Del.

[73] Assignee: E. I. Du Pont de Nemours and Company, Wilmington, Del.

[21] Appl. No.: 103,061

[22] Filed: Dec. 14, 1979

[51] Int. Cl.$^3$ .............................................. C01B 15/02
[52] U.S. Cl. ..................................... 423/591; 568/321
[58] Field of Search ......................... 260/591; 423/591; 568/321

[56] References Cited

U.S. PATENT DOCUMENTS

| | | | |
|---|---|---|---|
| 2,479,111 | 8/1949 | Harris | 423/591 |
| 2,819,949 | 1/1958 | Keeler et al. | 423/591 |
| 2,869,989 | 1/1959 | Keeler et al. | 423/591 |
| 2,871,103 | 1/1959 | Skinner et al. | 423/591 |
| 2,871,104 | 1/1959 | Rust | 423/591 |
| 2,910,415 | 10/1959 | Mashio et al. | 204/158 R |

FOREIGN PATENT DOCUMENTS 708339  5/1954  United Kingdom .
871830  7/1961  United Kingdom .

OTHER PUBLICATIONS

Russell et al., Oxidation of Organic Compounds", vol. I, "Advances in Chemistry Series 75, edited by F. R. Mayo, American Chemical Society, (1968), pp. 174–189.
Kato and Mashio, Kyoto Kogei Senli Daigaku, Kogeigakubu Memoirs of the Faculty of Industrial Arts, Kyoto Technical University, Science and Technology, Kyoto 23–40, (1963), No. 12.

*Primary Examiner*—Earl C. Thomas
*Assistant Examiner*—Wayne A. Langel

[57] ABSTRACT

Process comprising contacting and reacting a diarylmethanol having 13 to 25 carbon atoms and of the formula RCHOHR' wherein each of R and R' is aryl, the same or different, in the liquid state, at a temperature of about 130°–260° C., with gaseous oxygen to produce hydrogen peroxide and diaryl ketone of the formula RCOR' wherein R and R' are the same as above.

10 Claims, No Drawings

PREPARATION OF HYDROGEN PEROXIDE

DESCRIPTION

Technical Field

This invention relates to the preparation of hydrogen peroxide.

Background

Hydrogen peroxide is a valuable industrial chemical. Demand for this chemical in the United States in 1975 has been estimated at 72,000 tons (65,000 metric tons). Included among the many uses for the compound are: for bleaching, as a reagent for making industrial organic chemicals, and for treating water and sewage.

The preparation of hydrogen peroxide by the reaction of oxygen with secondary alcohols is well known. U.S. Pat. No. 2,479,111 discloses carrying out this process in the vapor phase. Liquid-phase processes are described in U.S. Pat. Nos. 2,819,949 and 2,871,104. Other patents disclose various aspects of this process. The most commonly used alcohol is isopropyl alcohol, from which acetone is formed as the principal organic by-product. U.S. Pat. No. 2,871,104 and its earlier partial counterpart British Pat. No. 708,339 disclose the reaction of gaseous oxygen with a secondary alcohol in the liquid phase at about 70° C. or higher to produce hydrogen peroxide. The hydrogen peroxide thus generated remains, collects, or accumulates in the liquid body that is undergoing oxidation. It may be recovered by withdrawing liquid oxidation product either continuously or intermittently from the reaction zone and fractionally distilling or otherwise treating the withdrawn product to recover the hydrogen peroxide from it. A small amount of hydrogen peroxide or an organic peroxide can be used in the initial reaction mixture as an initiator, particularly when a highly purified secondary alcohol is used.

By and large, these processes do not require the presence of an added catalyst, although the optional use of such a catalyst is disclosed in the art. Catalytic processes for preparing hydrogen peroxide by oxidation of alcohols are described, for example, in U.S. Pat. No. 2,910,415 and British Pat. No. 871,830.

A problem which is common to all the foregoing processes is that the mixture includes hydrogen peroxide, unreacted alcohol, the ketone that is formed as the principal organic by-product, any other organic by-products, and the catalyst, if one is used. One or more separation steps are required to isolate the hydrogen peroxide. Frequently, this is done by distillation, wherein the organic components of the mixture, which are usually more volatile, are distilled off, with a solution of hydrogen peroxide in water remaining. Besides adding expense and being time-consuming, this operation involves the possibilities of decomposition of the hydrogen peroxide and its reaction with the organic materials in the mixture. The process of the present invention largely obviates such a separation step.

DISCLOSURE OF INVENTION

The invention resides in a process for making hydrogen peroxide. More particularly, it resides in a process for preparing hydrogen peroxide by the reaction of gaseous oxygen with a diarylmethanol. In a preferred embodiment, the diarylmethanol is benzhydrol (diphenylmethanol). The process involves simply bubbling gaseous oxygen, alone or diluted with an inert gas, through a molten diarylmethanol at elevated temperature. Hydrogen peroxide, formed by reaction of the oxygen with the diarylmethanol, is carried out of the liquid by the gas stream, leaving most of the organic material behind. The desired hydrogen peroxide can be easily obtained as an aqueous solution, the form in which it is commonly used, by passing the gas stream through water.

The process comprises contacting and reacting a diarylmethanol having 13 to 25 carbon atoms and of the formula RCHOHR' wherein each of R and R' is aryl, the same or different, in the liquid state, at a temperature of about 130°–260° C., with gaseous oxygen to produce hydrogen peroxide and diaryl ketone of the formula RCOR' wherein R and R' are the same as above. The diaryl ketone that is the principal organic product can be converted by known reduction processes to the corresponding diarylmethanol, which can then be used in the primary step. The latter, therefore, is the key step in a cyclic process for the production of hydrogen peroxide in which no organic material is consumed.

Under some conditions the bis(diarylmethyl) ether corresponding to the diarylmethanol appears as a by-product. The formation of such ethers can be inhibited by incorporating a small amount of a selected alkali metal phosphate salt with the diarylmethanol. Operable salts include sodium and potassium pyrophosphate, sodium and potassium triphosphate, disodium phosphate, and dipotassium phosphate.

It is not known, strictly speaking, whether the reaction between oxygen and the diarylmethanol takes place in the vapor phase, the liquid phase, or both. When a bubble of gaseous oxygen is enclosed in a hot liquid diarylmethanol, a small amount of diarylmethanol will almost certainly vaporize into the gas phase, and a small amount of oxygen will almost certainly diffuse into and dissolve in the liquid phase. Reaction could take place in either or both of these homogeneous oxygen/diarylmethanol phases. Although it has not been proven, it is believed that the reaction occurs predominantly just inside the liquid phase at the liquid/vapor interface. The art appears to suggest that when gaseous oxygen is reacted with a liquid organic substrate in this manner, the process is customarily and arbitrarily designated as a liquid-phase process. In this sense, therefore, the present process may be regarded as a liquid-phase process.

The diarylmethanols that are operable in the process of the invention are compounds containing at most about 25 carbon atoms and having the formula RCHOHR', where R and R' are the same or different and are aryl groups. An aryl group is defined as a monovalent radical formed conceptually by removal of a hydrogen atom from a hydrocarbon that is structurally composed entirely of one or more benzene rings. Examples of such hydrocarbons include benzene, biphenyl, terphenyl, naphthalene, phenylnaphthalene, and naphthylbenzene. It will be seen that each of R and R' can contain two fused benzene rings, one or more nonfused benzene rings, or both. The preferred diarylmethanol is benzhydrol, the compound in which R and R' are phenyl, which is easily made from benzophenone, a large-volume industrial chemical. Other diarylmethanols that can be used as starting materials in the process of the invention include 4-phenylbenzhydrol, 2-naphthyl-(phenyl)methanol, dinaphthylmethanol, bis(biphenyl)-methanol, and terphenylyl)phenyl)methanol. All these diarylmethanols are readily accessible through reduction of the corresponding diaryl ketones by conventional methods.

For convenience and to reduce the possibility of forming explosive mixtures, the oxygen used in the process is provided by air. However, higher concentrations of oxygen in an inert gas, such as nitrogen or argon, can be used.

The reaction temperature is not highly critical and can be between about 130° C. and about 260° C. The preferred range is about 150°-200° C. The reaction temperature should be at least slightly above the melting point of the diarylmethanol, in order to insure that a completely liquid state is maintained. For this reason, diarylmethanols melting no higher than about 200° C. are preferred. For high-melting diarylmethanols, a high-boiling inert solvent for the diarylmethanol can be added to provide an all-liquid system. By "inert solvent" is meant an organic solvent which is inert under the conditions of the oxidation reaction. By "high-boiling solvent" is meant a solvent having a boiling point at least as high as the reaction temperature. Examples of such solvents include diphenyl ether and biphenyl.

The process is most conveniently carried out at atmospheric pressure. Higher pressures, i.e., up to about 5 atmospheres, can be used to provide a higher rate of reaction if desired. However, higher pressures also increase the possibility of forming an explosive mixture. Subatmospheric pressures, i.e., down to about 0.5 atmosphere, can also be used but provide no advantage.

If an alkali metal phosphate salt of the type described above is used to inhibit the formation of bis(diarylmethyl) ethers, its concentration in the system can range from as high as about 10% by weight of the diarylmethanol to as low as about 0.1%, or even lower as long as the desired inhibitory function is realized. Usually the concentration is about 1–5%.

The process can be conducted by a semibatch or continuous method. The following examples were carried out in a semibatch manner wherein all the diarylmethanol was charged at the start, together with a phosphate inhibitor, if one was used, and air was passed continuously through the molten material with continuous removal of hydrogen peroxide. In a continuous operation, the process could be conducted in a series of staged reactors, in a flow reactor, or in other systems familiar to those skilled in the art.

In a semibatch operation it seems probable that, at least over a fairly wide range, the rate of formation of hydrogen peroxide will increase as the rate of passage of oxygen through the reaction mixture is increased. It is advantageous to introduce the oxygen as a relatively large number of small bubbles, to realize a relatively high area of interface between the gas and liquid phases.

The hydrogen peroxide is conveniently recovered from the gaseous product mixture by passing the exit gas into water, in which the peroxide dissolves. The hydrogen peroxide often can be used directly in a subsequent operation as the aqueous solution which is recovered herein. If a high degree of purification is desired, traces of organic material in the aqueous solution can be removed by extraction, e.g., with methylene chloride.

The following examples illustrate the process of the invention.

EXAMPLE 1

Benzhydrol (2 g) was placed in a stoppered 50-ml filter flask with a magnetic stirring bar covered with Teflon ® fluorocarbon resin. A glass tube for introducing oxygen was inserted through the stopper to the bottom of the flask. The side arm of the flask was attached by rubber tubing to a glass tube that dipped below the surface of a titanium sulfate/sulfuric acid solution used to test for the presence of hydrogen peroxide. This reagent was made by the procedure of Satterfield and Bonnell, *Anal. Chem.* 1955, 27, 1174. The test solution was made by dissolving 0.5 ml of the reagent in 5–10 ml of distilled water. The flask was heated in an oil bath at 195° C., stirring was started, and a stream of air was passed through the molten benzhydrol and then through the titanium solution at about 50 ml/min. The test solution very soon became yellow, indicating the presence of hydrogen peroxide. After 10–20 minutes the test solution was replaced by a fresh solution, and this replacement was repeated twice. All four test solutions became yellow. The visible spectrum of each solution showed the 410 nm maximum obtained by adding dilute aqueous hydrogen peroxide to a separate test solution. No color appeared when air was passed directly through a similar test solution for one hour. After the air was shut off and the reaction mixture was cooled, analysis by gc showed that the mixture contained both benzhydrol and benzophenone.

EXAMPLE 2

The apparatus was a test tube containing a two-hole stopper. A gas-inlet tube in one hole extended to the bottom of the test tube and was drawn out at that point to an 0.5-mm capillary. A gas-exit tube through the other hole led to the bottom of a collector liquid that comprised 4.0 g of the titanium sulfate reagent of Example 1 dissolved in 40 ml of water. The benzhydrol used in the reaction was obtained by recrystallizing commercially available material from 95/5 hexane/ethanol. Analysis by gc showed that the recrystallized material contained about 0.1% benzophenone.

Benzhydrol (2.0 g) was placed in the bottom of the test tube, the tube was heated in an oil bath at 194° C., and air was passed through the liquid benzhydrol at 50–100 ml/min for 30 minutes. Spectrophotometric analysis of the collector solution indicated that 0.22 mmol of hydrogen peroxide had been collected from the gas stream, i.e., hydrogen peroxide was produced at a rate of about 0.44 mmol per hour. Analysis by gc of the organic reaction mixture remaining in the tube indicated that it contained about 11% benzophenone and 89% benzhydrol. No di(benzhydryl) ether, i.e., bis(diphenylmethyl) ether, was detected. These data correspond to about a 17% yield of $H_2O_2$ based on the amount of benzophenone formed.

EXAMPLE 3

The procedure of Example 2 was repeated, except that the oil-bath temperature was 150° C. and the reaction time was 1.5 hours. Analyses indicated that 0.54 mmol (0.36 mmol/hr) of hydrogen peroxide had been collected and that the organic reaction mixture contained about 6% benzophenone and 94% benzhydrol. Traces (0.1% or less) of benzaldehyde and diphenylmethane were also found. These data correspond to about an 82% yield of $H_2O_2$ based on the benzophenone formed.

EXAMPLE 4

The procedure of Example 3 was repeated, except that 0.1 g of hydrated sodium pyrophosphate was crushed and dried under nitrogen in the test tube at 150° C. before the benzhydrol was added, and the reaction time was two hours. Analyses indicated that 0.03 mmol (0.015 mmol/hr) of hydrogen peroxide had been collected and that the organic reaction mixture contained 0.3% benzophenone, 99.7% benzhydrol and little or no di(benzhydryl) ether. These data correspond to about 90% yield of $H_2O_2$ based on the benzophenone formed. This figure is only approximate because of the low conversion of benzhydrol, thus providing only small amounts of $H_2O_2$ and benzophenone.

EXAMPLE 5

Using the apparatus of Example 2, air was passed through 1.0 g of liquid recrystallized benzhydrol at 196° C. at 78 ml/min for 7 hours and 51 minutes. The collector liquid was a solution of 0.1 g of sodium pyrophosphate hydrate in 40 ml of water. Analyses indicated that 1.6 mmol of hydrogen peroxide (0.2 mmol/hr) had been collected, and that the organic reaction mixture contained 46% benzophenone, 51% benzhydrol, and 3% di(benzhydryl) ether. Traces of benzaldehyde, phenol, diphenylmethane, and benzyl alcohol were also found. These data correspond to a 29% yield of $H_2O_2$ based on the benzophenone formed.

EXAMPLE 6

The procedure of Example 5 was repeated, except that 0.1 g of sodium pyrophosphate hydrate was crushed and dried under nitrogen in the test tube before the benzhydrol was added. The air flow was 80 ml/min, and the reaction time was 7 hours and 40 minutes. Analyses indicated that 3.3 mmol of hydrogen peroxide (0.43 mmol/hr) had been collected, and that the organic reaction mixture contained about 72% benzophenone, about 28% benzhydrol, and 0.5% di(benzhydryl)ether. Traces of benzaldehyde, phenol, and diphenylmethane were also found. These data correspond to an 82% yield of $H_2O_2$ based on the benzophenone formed.

Inspection of the results of Examples 3–6 suggests that the presence of sodium pyrophosphate is more beneficial at 196° C. than at 150° C.

EXAMPLE 7

The starting material for this example was commercially available benzhydrol that had been washed with about 1 liter of water, dried, and recrystallized from hexane/ethanol as in Example 2. Gc analysis showed no material other than benzhydrol present. The reactor used was the same as that of Example 2.

The reactor was charged with 1.0 g of benzhydrol and 0.1 g of sodium pyrophosphate that had been dried under nitrogen. The tube was heated in an oil bath at 245° C., and air was passed through the liquid at 80 ml/min for 30 minutes. The collector solution was the same as in Example 2. Analyses indicated that 0.2 mmol of hydrogen peroxide (0.4 mmol/hr) had been collected, and that the organic reaction mixture contained 15% benzophenone and 85% benzhydrol. These data correspond to about a 24% yield of $H_2O_2$ based on the benzophenone formed.

EXAMPLE 8

The starting material for this example was 4-biphenylyl(phenyl)methanol, i.e., 4-phenylbenzhydrol, that was prepared by reducing 4-benzoylbiphenyl with sodium borohydride in ethanol. Gc analysis indicated that the product contained about 9.9% of unreacted 4-benzoylbiphenyl. The reactor used was the same as that of Example 2.

The reactor was charged with 1.0 g of 4-biphenyl(phenyl)methanol and 0.1 g of sodium pyrophosphate that had been dried under nitrogen. The tube was placed in an oil bath at 197° C., and air was passed through the liquid for 2 hours at 80 ml/min. The collector solution was the same as in Example 2. Analyses indicated that 0.2 mmol of hydrogen peroxide (0.1 mmol/hr) had been collected and that the organic reaction mixture contained about 38% 4-benzoylbiphenyl and 62% 4-biphenylyl(phenyl)methanol. These data correspond, after allowance is made for the 4-benzoylbiphenyl present in the starting material, to approximately an 18% yield of $H_2O_2$ based on the 4-benzoylbiphenyl formed.

EXAMPLE 9

The starting material for this example was 2-naphthyl(phenyl)methanol that was prepared by reduction of 2-benzoylnaphthalene with sodium borohydride in ethanol, followed by recrystallization of the product from hexane/ethanol. The reactor used was the same as that of Example 2.

The reactor was charged with 1.0 g of 2-naphthyl(phenyl)methanol and 0.1 g of sodium pyrophosphate that had been dried under nitrogen. The tube was placed in an oil bath at 190° C., and air was passed through the system into the collector liquid (the same as in Example 2) at 80 ml/min for 2 hours and 10 minutes. Spectrophotometric analysis indicated that about 0.02 mmol of hydrogen peroxide (about 0.1 mmol/hr) had been collected. Analysis by infrared indicated that the amount of 2-benzoylnaphthalene in the organic reaction mixture had increased.

Best Mode For Carrying Out The Invention

The best mode for practicing the process of the invention is believed to be illustrated in Example 6.

Industrial Applicability

The industrial applicability of the process of this invention is readily apparent from the known industrial uses for hydrogen peroxide.

I claim:

1. Non-catalytic process for preparing hydrogen peroxide, which process comprises contacting and reacting a diarylmethanol having 13 to 25 carbon atoms and of the formula RCHOHR' wherein each of R and R' is aryl, the same or different, in the liquid state, at a temperature of about 130°–260° C., with a gas stream containing oxygen to produce hydrogen peroxide and diaryl ketone of the formula RCOR' wherein R and R' are the same as above, which hydrogen peroxide is carried out of the liquid by the gas stream.

2. Process of claim 1 carried out in the presence of such an amount of alkali metal phosphate as is necessary to inhibit the formation of the bis(diarylmethyl) ether corresponding to the diarylmethanol.

3. Process of claim 2 wherein the amount of alkali metal phosphate is 1–5 wt. % of the amount of diarylmethanol.

4. Process of claim 1 wherein the diaryl ketone, after being separated from the hydrogen peroxide, is reduced to the corresponding diarylmethanol and the diarylmethanol is contacted and reacted with oxygen in the process of claim 1.

5. Process of claim 4 wherein the diaryl ketone is benzophenone.

6. Process of claim 1 wherein the hydrogen peroxide is collected in water.

7. Process of claim 1 wherein the temperature is about 150°–200° C.

8. Process of claim 1 carried out in the presence of an inert solvent for the diarylmethanol.

9. Process of claim 1 which is carried out in the absence of an inert solvent for the diarylmethanol.

10. Process of claim 1 wherein the diarylmethanol is benzhydrol.

* * * * *